United States Patent
Yu et al.

(10) Patent No.: US 12,357,993 B2
(45) Date of Patent: Jul. 15, 2025

(54) MICROFLUIDIC DEVICE FOR DIGITAL DROPLET PCR

(71) Applicant: Shenzhen Biorain Biotechnology Co.,Ltd., Guangdong (CN)

(72) Inventors: Linfen Yu, Guangdong (CN); Wei Yang, Guangdong (CN)

(73) Assignee: Shenzhen Biorain Biotechnology Co., Ltd., Shenzhen (CN)

( * ) Notice: Subject to any disclaimer, the term of this patent is extended or adjusted under 35 U.S.C. 154(b) by 674 days.

(21) Appl. No.: 17/511,821

(22) Filed: Oct. 27, 2021

(65) Prior Publication Data

US 2022/0126295 A1     Apr. 28, 2022

(30) Foreign Application Priority Data

Oct. 27, 2020 (CN) .......................... 202011165539.4
Aug. 25, 2021 (CN) .......................... 202122020826.2

(51) Int. Cl.
*B01L 3/00* (2006.01)
*C12Q 1/686* (2018.01)

(52) U.S. Cl.
CPC ........ *B01L 3/502784* (2013.01); *C12Q 1/686* (2013.01); *B01L 2200/027* (2013.01); *B01L 2200/0673* (2013.01); *B01L 2200/0689* (2013.01); *B01L 2300/0681* (2013.01)

(58) Field of Classification Search
CPC ......... B01L 3/502784; B01L 2200/027; B01L 2200/0673; B01L 2200/0684; B01L 2200/0689; B01L 2200/06; B01L 2200/10; B01L 2300/0681; B01L 2300/087; B01L 2300/0887; C12Q 1/686; C12Q 2563/159; C12Q 2565/629; G01N 21/6458
See application file for complete search history.

(56) References Cited

U.S. PATENT DOCUMENTS

2016/0271576 A1* 9/2016 Arab ..................... C12Q 1/686

FOREIGN PATENT DOCUMENTS

| CN | 109825426 A | * | 5/2019 |
| CN | 112121875 A | | 12/2020 |
| CN | 112871226 A | | 6/2021 |
| CN | 113117770 A | | 7/2021 |
| CN | 113275048 A | | 8/2021 |

OTHER PUBLICATIONS

Espacenet English Machine Translation of CN109825426A. (Year: 2019).*

* cited by examiner

*Primary Examiner* — Kathryn Elizabeth Limbaugh

(57) ABSTRACT

A microfluidic device, including: a main body, a sealing layer and a plurality of Polymerase Chain Reaction (PCR) units arranged on the main body. Each PCR unit includes a microchannel arranged on a surface of the main body, and a sample reservoir, an oil reservoir, a droplet generation zone, a transition zone, a droplet storage zone and a collection zone that are communicated with each other through the microchannel. The sealing layer is arranged on the surface of the main body to seal the main body. After generated, the droplets are collected in the oil reservoir and then distributed to the droplet storage zone through the transition zone.

10 Claims, 13 Drawing Sheets

MICROFLUIDIC DEVICE FOR DIGITAL DROPLET PCR

CROSS-REFERENCE TO RELATED APPLICATIONS

This application claims the benefit of priority from Chinese Patent Application Nos. 202011165539.4 and 202122020826.2, respectively filed on Oct. 27, 2020 and Aug. 25, 2021. The content of the aforementioned application, including any intervening amendments thereto, is incorporated herein by reference in its entirety.

TECHNICAL FIELD

This application relates to microfluidic chip techniques, and more specifically to a microfluidic device for digital droplet Polymerase Chain Reaction (PCR).

BACKGROUND

Traditional digital PCR is a method of absolute nucleic acid quantification based on the partitioning of individual analyte molecules into many replicate reactions at limiting dilution, resulting in one or zero molecules in most reactions. After end-point PCR, the starting concentration of template is determined by Poisson statistical analysis of the number of positive (containing amplified target) and negative (no amplified target detected) reactions. The digital PCR concept has many potential advantages over real-time PCR, including the capability to obtain absolute quantification without external references and robustness to variations in PCR efficiency.

Currently, there are 3 main digital droplet PCR platforms: microfluidic-chamber-based BioMark® dPCR from Fluidigm, micro-well chip-based QuantStudio12k flex dPCR from Life Technologies, and droplet-based ddPCR (ddPCR) QX200 from Bio-Rad®. Over these three methods, the droplet-based dPCR has main advantages over other two methods. First, the droplet-based dPCR usually has approximately 20,000 to 10,000,000 partitioned droplets per reaction which has higher sensitivity and accuracy than other two dPCR platforms. Secondly, the droplet-based dPCR can realize high throughput and low price. However, for most of the existing droplet-based dPCR systems, the droplet generation, PCR reaction and droplet detection are performed separately on different instruments.

SUMMARY

The aim of the present invention is that of remedying some drawbacks of the previous methods, such as avoiding droplets transfer from one vessel to another, integrating droplets generation, PCR, and preferentially fluorescent detection all in one device, reducing the high cost of current method and increasing analysis throughput.

Provided herein is a microfluidic device that includes at least one device for generating a quantity of droplets of a solution in low density oil and at least one storage zone for storing droplets at monolayer for PCR reaction and fluorescence imaging.

A further aim of the present invention is to provide a microfluidic device suitable for conducting digital PCR using droplets that is simpler, more effective and less costly, and requires less training of the operators to implement the process. An object of the present disclosure is to provide a microfluidic device for digital droplet PCR (ddPCR), in which the droplets are first generated in an oil phase tank, and then distributed to a droplet storage zone through a transition zone instead of being not directly distributed on the droplet storage zone after generated. Compared with the existing chip, the present disclosure overcomes the interference of bubbles to the droplet distribution, and also avoids the oil shortage during the droplet generation process.

The technical solutions of the present disclosure are described as follows.

The present disclosure provides a microfluidic device, comprising:
a main body;
a sealing layer; and
a plurality of Polymerase Chain Reaction (PCR) reaction units arranged on the main body;
wherein each of the plurality of PCR reaction units comprises at least one microchannel arranged on a surface of the main body, and a sample reservoir, an oil reservoir, a droplet generation zone, a transition zone, a droplet storage zone and a collection zone; the sample reservoir, the oil reservoir, the droplet generation zone, the transition zone, the droplet storage zone and the collection zone are communicated with each other through the at least one microchannel; the sealing layer is bonded with a bottom surface of the main body to seal the at least one microchannel;
the sample reservoir is configured to inject a dispersed phase;
the oil reservoir and the collection zone are configured to inject a continuous phase; the droplet generation zone is configured to form a plurality of droplets from the dispersed phase through the continuous phase; and
the plurality of droplets are configured to pass through the transition zone to be distributed on the droplet storage zone for PCR amplification and optical detection.

In an embodiment, the main body comprises an upper layer and a lower layer;
the sample reservoir, the oil reservoir and the collection zone are arranged on the upper layer; and
the at least one microchannel, the droplet generation zone, the transition zone and the droplet storage zone are arranged on the lower layer.

The droplets are formed in multiple parallelized microchannels by step emulsification where the dispersed phase is injected and the drop detachment is due to a local loss of equilibrium under the force due to surface tension. The parallelized microchannel which is called nozzle is triangular in its shape with its cross-section gradually increasing until it reaches the storage zone where the height abruptly increases. This nozzle results in drop formation through a static instability that is determined solely by the device geometry.

In embodiment, the sample reservoir is provided with a sample injection hole; and the sample injection hole is connected to the lower layer of the main body and is communicated with the droplet generation zone.

In an embodiment, the droplet generation zone comprises a dispersed phase inlet, a dispersed phase flow channel and a plurality of parallelized nozzles; the dispersed phase flow channel is communicated with the dispersed phase inlet and the plurality of nozzles; and the dispersed phase flows through the dispersed phase flow channel to enter the plurality of nozzles to generate the plurality of droplets;

the dispersed phase inlet is provided on the lower layer of the main body, and is communicated with the sample reservoir; and the plurality of nozzles are communicated with the transition zone.

The device is initially filled with the liquid (generally oil with a surfactant which can stabilize the droplets) that will form the continuous phase. The dispersed fluid is then injected into the reservoir through the inlet channel. The droplet is pinched off when the dispersed fluid flows into the nozzle and is led to the storage zone by the change of the Laplace pressure force. Due to the abrupt increase of height from the nozzle to the droplet storage zone, the Laplace pressure force implies a lower pressure of the continuous phase in the nozzle than in the storage zone.

In an embodiment, each of the plurality of nozzles is configured as a triangle reservoir that extends to the droplet storage zone; each of the plurality of nozzles has a height of 1-50 µm; and a height of the droplet storage zone is equal to or large than 5 times the height of each of the plurality of nozzles.

In an embodiment, the transition zone comprises a first storage slot arranged on the lower layer of the main body; the oil reservoir is provided with a first oil injection hole; and the first oil injection hole is communicated with the first storage slot.

In an embodiment, the droplet storage zone comprises a second storage slot and a first filtration zone; the second storage slot is arranged on the lower layer of the main body, and is communicated with the first storage slot; and the first filtration zone is arranged in the second storage slot.

In an embodiment, a depth of the first storage slot is greater than or equal to 1.5 times a depth of the second storage slot, and the depth of the second storage slot is greater than or equal to 1.2 times a diameter of each of the plurality of droplets.

In an embodiment, the collection zone is provided with a second oil injection hole and an oil injection channel;
the second oil injection hole is communicated with the lower layer of the main body; and
the oil injection channel is configured for communicating the second oil injection hole with the second storage slot.

In an embodiment, the lower layer of the main body is further provided with a second filtration zone; and the second filtration zone is communicated between the oil injection channel and the second storage slot.

The present disclosure also provides a microfluidic device, comprising:
an upper layer; and
a sealing cover;
wherein an upper surface of the upper layer of the microfluidic device is provided with a sample reservoir and a collection zone, and a lower surface of the upper layer of the microfluidic device is provided with a droplet generation zone and a droplet storage zone;
the sample reservoir is communicated with the droplet generation zone; the droplet generation zone is communicated with the droplet storage zone; and the droplet storage zone is communicated with the collection zone;
the droplet generation zone and the collection zone are both provided with the sample reservoir; and the sealing cover is configured to cover the sample reservoir; and
the sample reservoir is provided with an aqueous phase tank, and is configured to inject a sample phase; the sample phase is configured to flow into the droplet generation zone; the droplet generation zone is configured to transform the sample phase into a plurality of droplets; and the plurality of droplets are configured to flow into and spread on the droplet storage zone.

In an embodiment, the microfluidic device further comprises a lower layer; a lower surface of the lower layer of the microfluidic device is provided with a sealing layer; the droplet generation zone and the droplet storage zone are both configured as a microchannel; and the sealing layer is configured to seal a main body of the microfluidic device.

In an embodiment, the microfluidic device further comprises a filtration zone; the droplet storage zone is communicated with the collection zone through the filtration zone.

In an embodiment, a depth of the droplet storage zone is greater than or equal to 1.1 times a diameter of each of the plurality of droplets.

In an embodiment, the sample reservoir comprises a sample reservoir main body and a sample injection hole; the sample reservoir main body is arranged on the upper surface of the upper layer of the microfluidic device; the sample injection hole is arranged on a top of the sample reservoir main body; and the sample injection hole is communicated with the droplet generation zone.

In an embodiment, the droplet generation zone comprises a sample injection channel, a dispersed phase flow channel and a plurality of sample phase branch channels;
the sample injection channel is communicated with the sample reservoir;
the dispersed phase flow channel is communicated with the sample injection channel; and
the plurality of sample phase branch channels are communicated with the dispersed phase flow channel and the droplet storage zone.

In an embodiment, the plurality of sample phase branch channels are arranged side by side; both ends of each of the plurality of sample phase branch channels are respectively provided with a nozzle; and each of the plurality of sample phase branch channels is communicated with the dispersed phase flow channel and the droplet storage zone through nozzles.

In an embodiment, the droplet storage zone comprises a storage slot and a filtration zone; the filtration zone is arranged in the storage slot; and a depth of the storage slot is greater than or equal to 1.1 times a diameter of each of the plurality of droplets.

In an embodiment, the filtration zone comprises a plurality of interception channels; a waste fluid flow channel and a waste liquid discharge channel;
the waste fluid flow channel is communicated with the plurality of interception channels;
the waste liquid discharge channel is communicated with the waste fluid flow channel and the collection zone; and
the waste liquid discharge channel is provided with a plurality of filter microcolumns.

In an embodiment, the collection zone comprises a waste liquid storage cup and a waste liquid hole; the waste liquid hole is arranged in the waste liquid storage cup, and is communicated with the waste liquid discharge channel.

Compared to the prior art, the present disclosure has the following beneficial effects.
1) The oil reservoir is designed to have an open-type structure, such that the oil can be fed when the droplets are generated to avoid the oil shortage, so as to render the droplets uniform in size. Moreover, since the top of the oil phase tank is open, the bubbles generated during the droplet generation process all float up to the top of the oil phase tank to be discharged instead of entering the droplet storage zone.

2) The oil can be fed through the oil reservoir and the collection zone before use, and thus there is no need to pre-fill the chip with oil, facilitating the transportation and storage.

3) The sample reservoir, the oil reservoir and the collection zone located on the upper layer of the main body and the microchannel on the lower layer of the main body are integrally injection molded, and sealed by the sealing layer. In this case, the microchannel can be tightly sealed; and moreover, it can greatly reduce the cost of injection molding and simplify the manufacture process.

(4) The design of the device includes one sample reservoir, as least one droplets generation channel with nozzles, at least one storage zone for holding the droplet, and one outlet. It is suitable for ddPCR where the various steps are carried out in a single microfluidic device.

(5) The design of microchannels with a nozzle in the device is suitable for uniformly generating droplets by step emulsification techniques.

(6) The droplet generating oil is introduced into microdevices in advance, where the droplets are detached at the junction of microchannel and droplet storage zone, by the surface tension of the solution. Advantageously, the droplets size is not affected by the velocity of the oil as the oil is static in the storage zone.

(7) Introducing a low-density oil (the density of oil is lower than water, such as silicone oil or mineral oil). Preferentially, the sample is cover under the oil which can avoid liquid evaporation and sample cross contamination.

(8) Applying an especially surfactant in oil which can facilitate droplets generation evenly and avoid spontaneously droplets emerging when come into contact in storage zone.

(9) Advantageously, the bottom layer of the device was a thin and transparent plastic membrane through which the heat can be transferred efficiently and PCR can be performed directly in the storage zone. Preferentially, in this device, the temperature variation is applied to the entire microfluidic device containing the droplets.

(10) Advantageously, fluorescent imaging of droplets in the storage zone can be carried out in the storage zone as the droplets are distributed in monolayer, therefor the transfer of the droplets from one vessel to another are thus avoided to reduce the droplet loss.

The device is particularly suitable for implementing the ddPCR process effectively, and it can integrate producing droplets, and performing the thermocycling, and finally for analyzing the droplets after the thermocycling thereof all in one microfluidic device.

Figure 1:
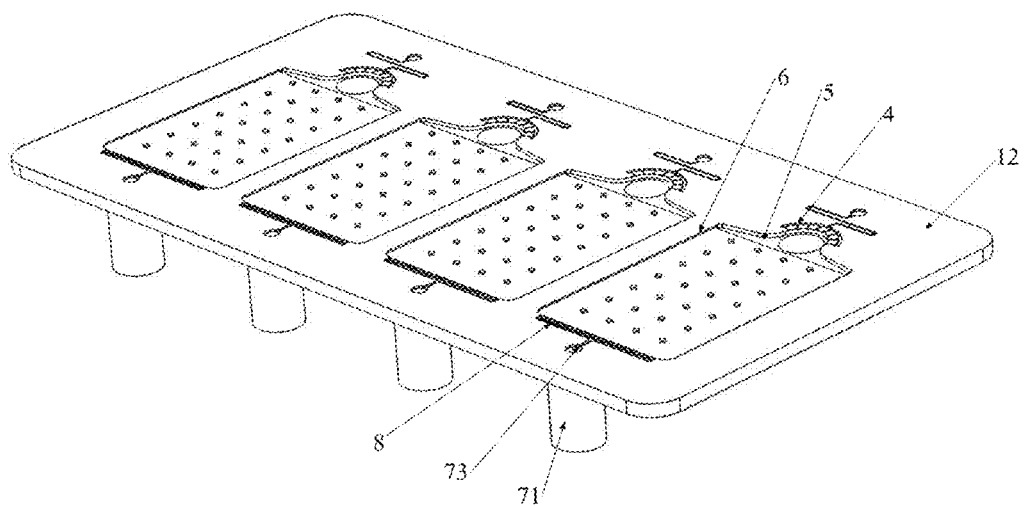
FIG. 1 is a perspective view of a microfluidic device according to an embodiment of the present disclosure.
Figure 2:
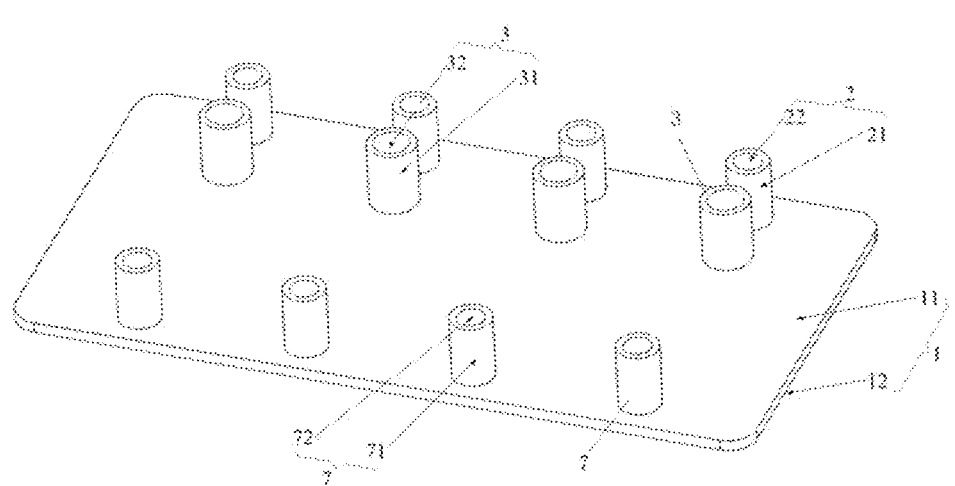
FIG. 2 is a perspective view of the microfluidic device from another perspective.
Figure 3:
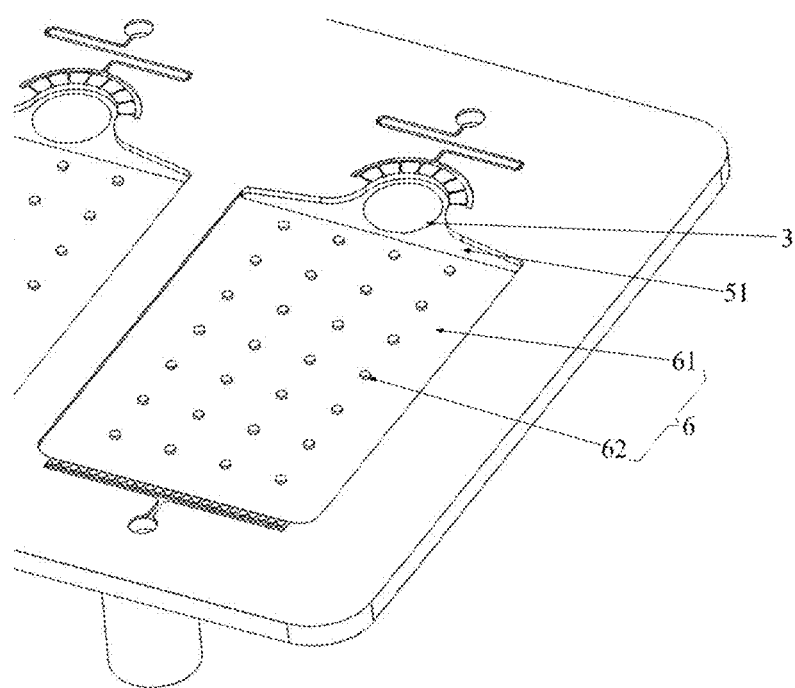
FIG. 3 is a partially-enlarged perspective view of a PCR unit according to an embodiment of the present disclosure.
Figure 4:
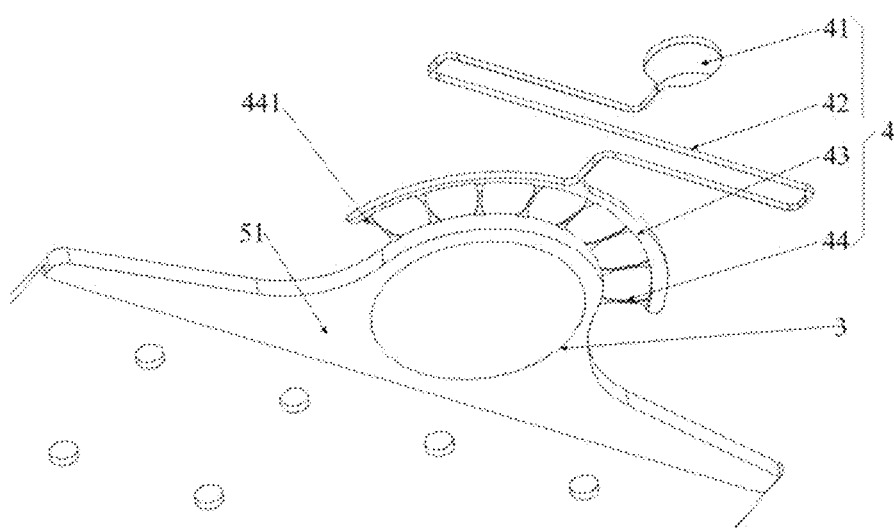
FIG. 4 is a partially-enlarged perspective view of a droplet generation zone according to an embodiment of the present disclosure.
Figure 5:
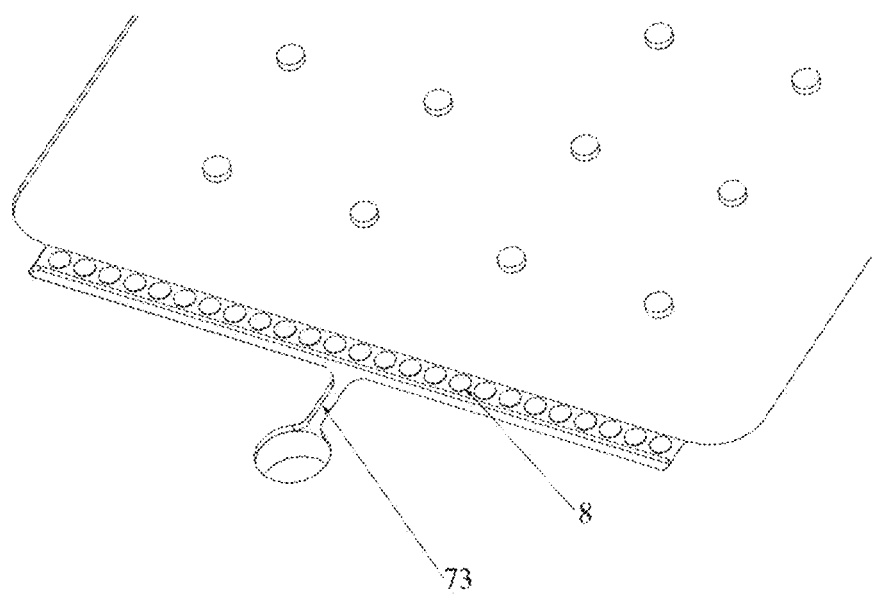
FIG. 5 is a partially-enlarged perspective view of a collection zone and a second filtration zone according to an embodiment of the present disclosure.
Figure 6:
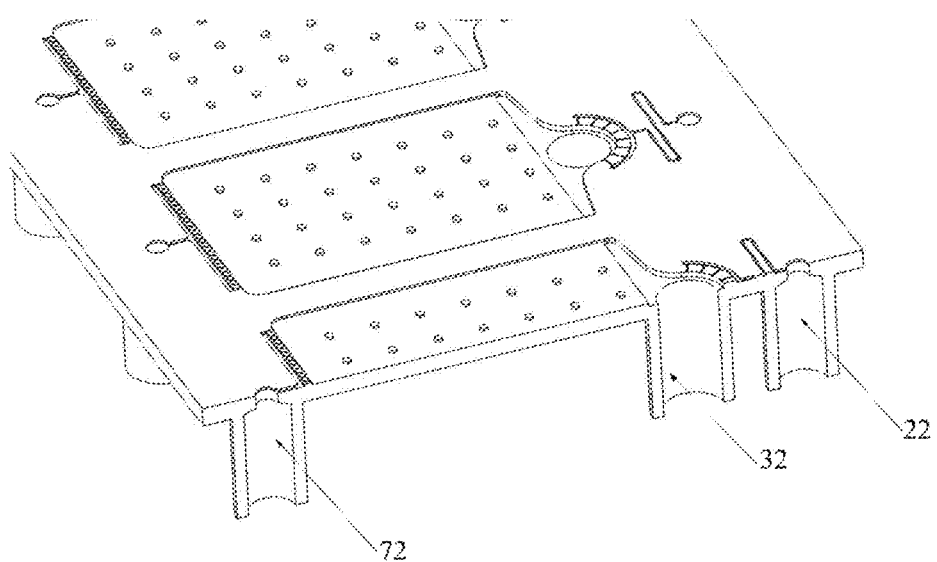
FIG. 6 is a partial cross-sectional view of the microfluidic device according to an embodiment of the present disclosure.

In the drawings:
1, main body;
2, sample reservoir; 3, oil reservoir;
4, droplet generation zone; 5, transition zone; 6, droplet storage zone;
7, collection zone; 8, second filtration zone;
11, upper layer; 12, lower layer;
13, sealing cover; 14, sealing layer;
21, sample reservoir main body; 22, sample injection hole;
31, first oil reservoir; 32, first oil injection hole;
41, dispersed phase inlet; 42, sample injection channel;
43, dispersed phase flow channel; 44, sample phase branch channel;
51, first storage slot;
61, second storage slot; 62, first filtration zone;
71, second oil reservoir; 72, second oil injection hole; 73, oil injection channel;
81, interception channel; 82, waste fluid flow channel; 83, waste liquid discharge channel; 84, filter microcolumn; and
441, nozzle.

DETAILED DESCRIPTION OF EMBODIMENTS

The technical solutions of the present disclosure will be described completely and clearly below with reference to the accompanying drawings and embodiments.

Embodiment 1

Referring to FIGS. 1-6, a microfluidic device is provided, which includes a main body 1, a sealing layer 14, and a plurality of Polymerase Chain Reaction (PCR) units arranged on the main body 1. Each of the plurality of PCR units includes at least one microchannel arranged on a surface of the main body 1, and a sample reservoir 2, an oil reservoir 3, a droplet generation zone 4, a transition zone 5, a droplet storage zone 6 and a collection zone 7. The sample reservoir 2, the oil reservoir 3, the droplet generation zone 4, the transition zone 5, the droplet storage zone 6 and the collection zone 7 are communicated with each other through the microchannel. The sealing layer is arranged on the surface of the main body 1, and is configured to seal the microchannel to prevent droplets in the microchannel from falling out. The sample reservoir 2 is configured to inject a dispersed phase. The oil reservoir 3 and the collection zone 7 are configured to inject a continuous phase. The droplet generation zone 4 is configured to form a plurality of droplets from the dispersed phase through the continuous phase; and the plurality of droplets are configured to pass through the transition zone 5 to be spread on the droplet storage zone 6 for PCR amplification and optical detection.

The main body 1 includes an upper layer 11 (an upper surface of the main body 1) and a lower layer 12 (a lower surface of the main body 1). The sample reservoir 2, the oil reservoir 3 and the collection zone 7 are arranged on the upper layer. The droplet generation zone 4, the transition zone 5 and the droplet storage zone 6 and the microchannel are arranged on the lower layer 12. The sample reservoir 2 and the collection zone 7 are respectively arranged on both sides of the oil reservoir 3. The droplet generation zone 4, the transition zone 5 and the droplet storage zone 6 are arranged in sequence to enable fluid to flow from the droplet generation zone 4 to the transition zone 5, and then reach the droplet storage zone 6. The sample reservoir 2 includes a sample reservoir main body 21 arranged on the upper layer 11 of the main body 1 and a sample injection hole 22 opened in the sample reservoir main body 21. The sample injection hole 22 is connected to the lower layer 12 of the main body 1, and is communicated with the droplet generation zone 4. The droplet generation zone 4 includes a dispersed phase inlet 41, a sample injection channel 42, a dispersed phase flow channel 43 and a plurality of sample phase branch channels 44. The dispersed phase inlet 41 is provided on the lower layer 12 of the main body 1, and is communicated with the sample injection hole 22. The sample injection channel 42 is communicated with the dispersed phase inlet 41. The dispersed flow channel 43 is communicated with the sample injection channel 42, and the plurality of sample phase branch channels 44 are communicated with the dispersed phase flow channel 43 and the transition zone 5. The microchannel includes the sample injection channel 42, the sample flow channel 43, the plurality of sample phase branch channels 44, a first storage slot 51 and a second storage slot 61. Specifically, the sample injection channel 42 has an "S" shape; and the plurality of sample phase branch channels 44 are arranged to form an arc, which matches an arc region of the transition zone 5.

Each of the plurality of sample phase branch channels 44 is communicated between the dispersed phase flow channel 43 and the transition zone 5 through two nozzles 441. The transition zone 5 includes the first storage slot 51 arranged on the lower layer 12 of the main body 1. One side of the first storage slot 51 close to the sample reservoir 2 has a symmetrical arc or a wave shape, and another side far away from the sample reservoir 2 (i.e., connected to the droplet storage zone 6) has a straight shape. Specifically, a slot wall on the side of the first storage slot 51 close to the sample reservoir 2 extends from an intersection with the droplet storage zone 6 to a direction of the first storage slot 51 approaching the sample reservoir 2 to form an arch shape. The side of the first storage slot 51 away from the sample reservoir 2 is roughly "Ω" shaped, and the wall on the side of the first storage slot 51 away from the sample reservoir 2 has a line shape, which is combined with the slot wall close to the sample reservoir 2 to form the first storage slot 51. The oil reservoir 3 includes a first oil reservoir 31 and a first oil injection hole 32. The first oil reservoir 31 is arranged on the upper layer 11 of the main body 1, and the first oil injection hole 32 is connected to the first storage slot 51. The droplet storage zone 6 includes a second storage slot 61 and a first filtration zone 62. The second storage slot 61 is arranged on the lower layer 12 of the main body 1, and is communicated with the first storage slot 51. The first filtration zone 62 is arranged in the second storage slot 61. A depth of the first storage slot 51 is greater than or equal to 1.5 times a depth of the second storage slot 61, and the depth of the second storage slot 61 is greater than or equal to 1.2 times a diameter of each of the plurality of droplets. The collection zone 7 includes a second oil reservoir 71, a second oil injection hole 72 and an oil injection channel 73. The second oil reservoir 71 is arranged on the upper layer 11 of the main body 1, and the second oil injection hole 72 is connected to the lower layer 12 of the main body 1. The oil injection channel 73 is configured for communicating the second oil injection hole 72 with the second storage slot 61. The lower layer 12 of the main body 1 is further provided with a second filtration zone 8; and the second filtration zone 8 is communicated between the oil injection channel 73 and the second storage slot 61.

The working principle of the present disclosure is described as follows.

Referring to FIGS. 1-6, in this embodiment, the main body 1 is provided with four groups of PCR reaction units which are independent to each other, and the four groups of PCR reaction units are arranged in parallel and spaced apart. Each of the PCR reaction units corresponds to a sample, and can individually complete all processes such as droplet generation, droplet storage, droplet distribution, PCR thermal cycle and fluorescence imaging, with a high efficiency. The number of the PCR reaction units can also be adjusted according to actual needs. The sealing layer can be a thin film with a thickness of less than 1 mm, and can be sealed to the surface of the lower layer 12 of the main body 1 by bonding, welding, thermocompression bonding, chemical bonding and so on to seal the microchannel, thereby ensuring a tightness of the seal. The principle of one of the PCR reaction units is now explained, and the working principles of other PCR reaction units are the same.

As shown in FIGS. 3-6, the dispersed phase can be injected through the sample injection hole 22. The dispersed phase is configured to flow into the dispersed phase flow channel 43 through the dispersed phase inlet 41 and the sample injection channel 42. In this embodiment, the dispersed phase flow channel 43 is in an arc shape, and an arc-shaped mouth of the dispersed phase flow channel 43 is arranged in a direction of the droplet storage zone 6. The plurality of sample phase branch channels 44 are communicated with the dispersed phase flow channel 43 and the first storage slot 51 of the transition zone 5. Both ends of each of the plurality of sample phase branch channels 44 are respectively provided with a nozzle 441. The nozzle 441 is a symmetrical dual-beveled nozzle or a single-beveled nozzle. An angle of the nozzle 441 is greater than 5°, preferably 5° to 120°. The number of the nozzles is 441 preferably 1-40. When the dispersed phase flows into the oil reservoir 3 containing the continuous phase (oil) through the nozzle 441, the dispersed phase is broken into droplets with the same size under the action of pressure difference and surface tension (principle of step emulsification). Then the droplets are wrapped in oil and stored in the oil reservoir 3. In this embodiment, the number of the plurality of nozzles 441 is set to 8, and the more the nozzles 441 are set, the higher the droplet generation efficiency is reached. The oil reservoir 3 is designed to have an open-type structure. The bubbles generated during the droplet generation process all float up to the top of the oil reservoir 3 (the density of the oil used is lighter than that of water, which can ensure that the droplets sink and the bubbles rise), thereby ensuring that the bubbles do not flow into the droplet storage zone 6.

After the droplets are generated, the droplets are first stored in the oil reservoir 3, and then are allowed to flow evenly into the second storage slot 61 of the droplet storage zone 6 through the first storage slot 51 of the transition zone 5. In order to ensure the rapid and uniform monolayer distribution of the droplets from the transition zone 5 to the droplet storage zone 6, the depth of the first storage slot 51 of the transition zone 5 is designed to be greater than or equal to 1.5 times the depth of the second storage slot 61 of the droplet storage zone 6, and the depth of the second storage slot 61 of the droplet storage zone 6 is designed to be greater than or equal to 1.2 times the diameter of the droplets, thereby ensuring the monolayer distribution of the droplets. One side of the main body 1 with a thin film is heated to realize a PCR thermal cycle of the droplets in the droplet storage zone 6, and subjected to fluorescence imaging detection. The first filtration zone 62 in the droplet storage zone 6 and the second filtration zone 8 communicated between the oil injection channel 73 and the droplet storage zone 6 both include a plurality of microcolumns, which can intercept impurities.

The present disclosure is performed through the following steps.
1) The oil is added to the second oil reservoir 71 through the second oil injection hole 72, and the droplet storage zone 6 is filled quickly with the oil phase.
2) The oil is added to the first oil reservoir 31 through the first oil injection hole 32, and the dispersed phase is added to the sample reservoir main body 21 through the sample injection hole 22. The dispersed phase is allowed to pass through the plurality of nozzles 441 of the droplet generation zone 4 under the action of pressure, and broke into droplets with the same size by the step emulsification, which then flow into the transition zone 5.
3) The droplets (the dispersed phase is wrapped in oil) generated are first stored in the oil reservoir 3, and then enter into the droplet storage zone 6 evenly and quickly through the transition zone 5 to achieve the monolayer distribution of the droplets.
4) The side of the main body 1 with the thin film is heated to realize the PCR thermal cycle of the droplets in the droplet storage zone 6, and subjected to fluorescence imaging detection.

Embodiment 2

Figure 7:
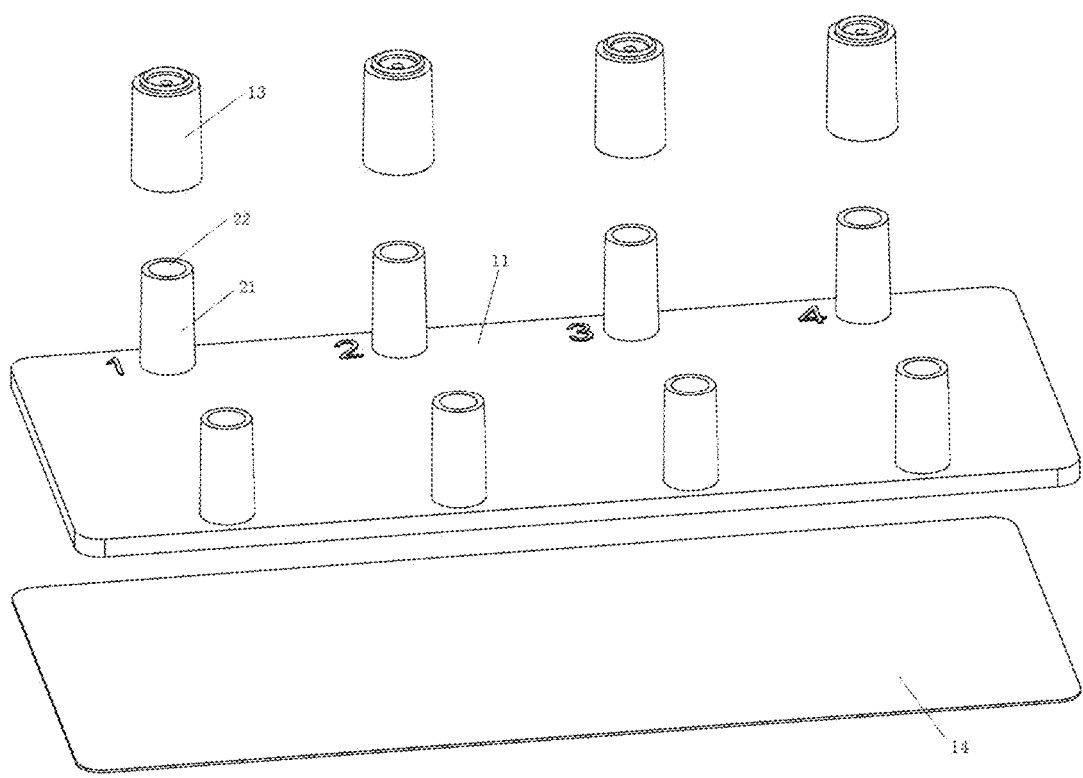
FIG. 7 schematically depicts a structure of the microfluidic device according to another embodiment of the present disclosure.
Figure 8:
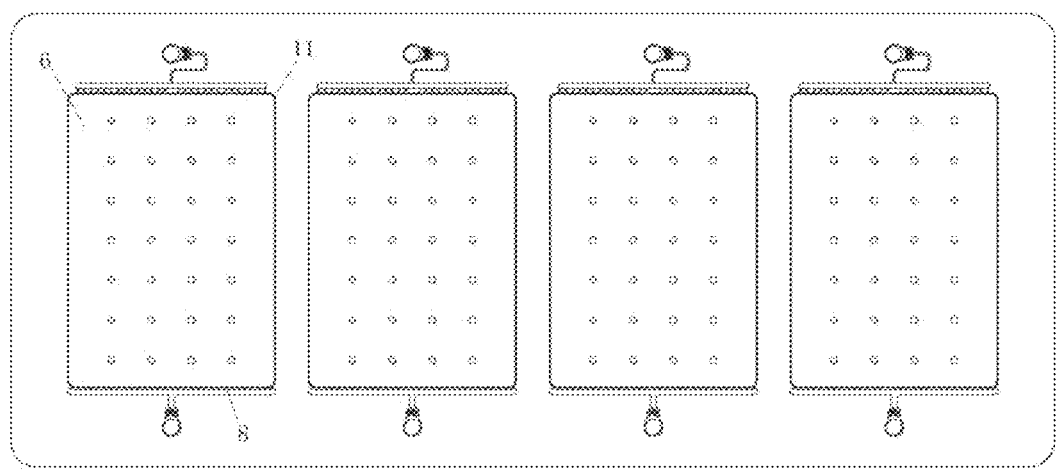
FIG. 8 is a schematic diagram of a structure of a lower surface of an upper layer of the main body according to another embodiment of the present disclosure.
Figure 9:
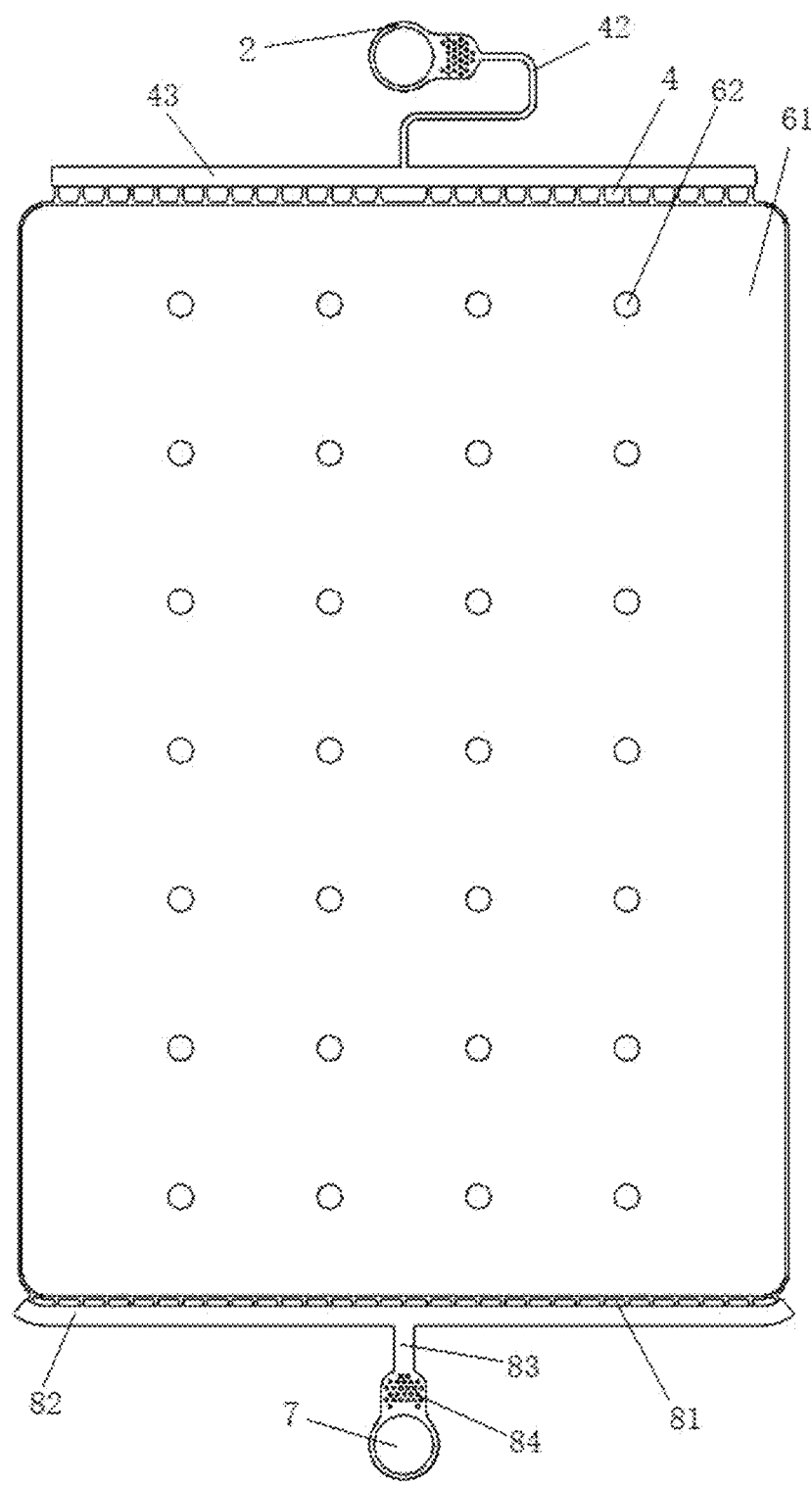
FIG. 9 is another schematic diagram of the structure of the lower surface of the upper layer of the main body according to another embodiment of the present disclosure.

As shown in FIGS. 7-9, a microfluidic device includes an upper layer 11. An upper surface of the upper layer 11 of the microfluidic device is provided with a sample reservoir 2 and a collection zone 7, and a lower surface of the upper layer 11 of the microfluidic device is provided with a droplet generation zone 4 and a droplet storage zone 6. The sample reservoir 2 is communicated with the droplet generation zone 4; the droplet generation zone 4 is communicated with the droplet storage zone 6; and the droplet storage zone 6 is communicated with the collection zone 7. The sample reservoir 2 is provided with an aqueous phase tank, and is configured to inject a sample phase. The sample phase is configured to flow into the droplet generation zone 4. The droplet generation zone 4 is configured to transform the sample phase into a plurality of droplets; and the plurality of droplets are configured to flow into and spread on the droplet storage zone 6. Specifically, the collection zone 7 is configured for waste liquid storage. The collection zone 7 has an oil drain. The droplet detection is performed in the droplet storage zone 6, that is, the droplet storage zone 6 is a droplet detection zone. Specifically, the microfluidic device further includes a sample injection channel 42, a dispersed phase flow channel 43 and a plurality of sample phase branch channels 44. The sample injection channel 42 is communicated with the sample reservoir 2, the dispersed phase flow channel 43 is communicated with the sample injection channel 42, and the plurality of sample phase branch channels 44 are communicated with the dispersed phase flow channel 43 and the droplet storage zone 6. The plurality of sample phase branch channels 44 are arranged side by side; both ends of each of the plurality of sample phase branch channels 44 are respectively provided with a nozzle; and each of the plurality of sample phase branch channels 44 is communicated with the dispersed phase flow channel 43 and the droplet storage zone 6 through nozzles.

The sample injection channel 42 has multiple bends or the sample injection channel 42 is in a zigzag state, and the dispersed phase flow channel 43 is in a linear shape (i.e., a straight shape). The plurality of nozzles 441 are arranged to form a linear shape, which matches the linear shape of the dispersed phase flow channel 43. Specifically, compared to the Embodiment 1, the oil reservoir 3 is not provided in this embodiment, and the problem of air bubbles is solved by pre-filling with oil. The droplets generated from the droplet generation zone 4 are allowed to flow into the droplet storage zone 6 directly to prevent the droplet deformation and improve the distribution.

In an embodiment, the sample reservoir 2 includes a sample addition microchannel, a sample reservoir, and a sample outlet. A lower end of the sample reservoir 2 is inclined. The sample outlet is set at a sharp corner of the bottom of the sample reservoir 2. The sample outlet is in communication with the droplet generation zone 4. The collection zone 7 includes an air discharge passage and a waste reservoir. The air discharge passage is connected to the waste reservoir and an air discharge hole.

A microfluidic device further includes a lower layer. A lower surface of the lower layer of the microfluidic device is provided with a sealing layer 14. The droplet generation zone 4 and the droplet storage zone 6 are both configured as a microchannel, and the sealing layer is configured to seal the droplet generation zone 4 and the droplet storage zone 6. The microchannel is used for droplet generation and distribution. The sealing layer 14 is a thin film, and the lower surface of the upper layer 11 of the microfluidic device is attached to the thin film to form a closed microchannel structure and the droplet storage zone 6. The lower surface of the upper layer 11 of the microfluidic device is sealed with the thin film by adhesion, welding, hot-press bonding, chemical bonding and other methods to ensure a firm and tight bonding. Heating can be carried out from the surface of the thin film, and the thin film with a thickness of 100-600 μm, so that the droplets in the droplet storage zone 6 are subjected to PCR thermal cycle and fluorescence imaging detection in situ. Microchannels are arranged on both sides or the middle of the microfluidic device.

Specifically, the sample reservoir 2 is used to store the dispersed phase. The droplet generation zone 4 is used to transform the dispersed phase into tens of thousands to millions of droplets, for example, to transform the water phase sample into aqueous droplets wrapped by oil. The droplets are performed PCR reaction in the droplet storage zone 6. After the reaction is completed, fluorescence detection is performed by CCD imaging shooting.

The microfluidic device further includes a sealing cover 13. The sample reservoir 2 includes a sample reservoir main body 21 and a sample injection hole 22. The sample reservoir main body 21 is arranged on the upper surface of the upper layer of the microfluidic device; the sample injection hole 22 is arranged on a top of the sample reservoir main body 21; and the sample injection hole 22 is communicated with the droplet generation zone 4.

The droplet generation zone 4 and the collection zone 7 are both provided with a sample injection reservoir. A sealing cover 13 is configured to cover the sample injection reservoir. The sample injection reservoir is a raised reservoir for liquid storage.

The microfluidic device further includes a second filtration zone 8. The droplet storage zone 6 is communicated with the collection zone 7 through the second filtration zone 8. The second filtration zone 8 includes a plurality of interception channels 81, a waste fluid flow channel 82 and a waste liquid discharge channel 83. The waste fluid flow channel 82 is communicated with the plurality of interception channels 81, and the waste liquid discharge channel 83 is communicated with the waste fluid flow channel 82 and the collection zone 7. The waste liquid discharge channel 83 is provided with a plurality of second filter microcolumns 84.

A distance between the second filter microcolumns 84 is 10-100 μm, and a function of the second filter microcolumns 84 densely distributed is to intercept impurities. The second filtration zone 8 can be an interception area.

A depth of the droplet storage zone 6 is greater than or equal to 1.1 times a diameter of each of the plurality of droplets, so as to enable the monolayer distribution. The droplet storage zone 6 includes a second storage slot 61 and a first filtration zone 62. The first filtration zone 62 is arranged in the second storage slot 61. A depth of the second storage slot 61 is greater than or equal to 1.1 times a diameter of each of the plurality of droplets. The second storage slot 61 is a droplet spread slot, and the first filtration zone 62 is a first filter microcolumn.

In an embodiment, the collection zone 7 includes a waste liquid storage cup and a waste liquid hole. The waste liquid hole is arranged in the waste liquid storage cup, and is communicated with the waste liquid discharge channel 83.

The microfluidic device further includes a sealing ring. The sealing ring includes a circular ring connected by a connecting section. An upper and a lower end of the circular ring are provided with a single-ring or multiple-ring sealing ring. An inner wall of the circular ring is sleeved on a sample column.

The dispersed phase is preferably an aqueous phase, and the generation continuous phase and the detection continuous phase are preferably an oil phase. A density of the oil phase is lighter than a density of water, so that the droplets can sink and ensure that the droplets are not easily volatilized during heating.

In this embodiment, the operation process is to pre-feed the droplet generation oil to the microfluidic device, and complete the bubble discharge to ensure that there are no bubbles remaining in the entire zone of the microfluidic device. The sample phase is added in the sample reservoir 2 (aqueous phase tank), and then oil is injected above the sample phase. The sample phase is configured to flow into the dispersed phase flow channel 43 through the sample injection channel 42 communicated with the sample reservoir 2 under the action of pressure, and then the droplets generated are configured to flow into the droplet storage zone 6 through the plurality of sample phase branch channels 44. In this embodiment, the plurality of sample phase branch channels 44 are arranged side by side. The number of the plurality of sample phase branch channels 44 is 1-40.

Both ends of each of the plurality of sample phase branch channels 44 are provided with nozzles. The nozzle is a symmetrical dual-beveled opening or a single-beveled opening. An angle of the nozzle is 5°-120°. When the sample phase is configured to flow into the droplet storage zone 6 through the nozzle, the sample phase is broken into droplets (aqueous droplets wrapped by oil) with the same size under an action of pressure difference and surface tension (step emulsification), and the droplets are spread in the droplet storage zone 6. In order to ensure that the single layer of droplets is evenly spread in the droplet storage zone 6, the depth of the second storage slot 61 is designed to be greater than or equal to 1.1 times the diameter of the droplets, thereby ensuring the spread of the single layer of droplets. One side of the main body 1 with a thin film is heated to realize a PCR thermal cycle of the droplets in the second storage slot 61, and subjected to fluorescence imaging detection. After the detection is completed, the waste liquid is discharged into the waste liquid storage cup through the interception channel 81, the waste fluid flow channel 82 and the waste liquid discharge channel 83 in sequence.

The oil is used to cover on the top of the sample. The sample passes through a shallow channel of the droplet generation zone 4 under the action of pressure, and the droplets with the same size are generated through the step emulsification. The droplets generated are distributed uniformly and quickly to achieve the monolayer distribution in the droplet storage zone 6.

As shown in FIG. 7, the microfluidic device in this embodiment is provided with four groups of PCR reaction units which are independent to each other. The number of PCR reaction units can also be set freely according to actual needs. The four groups of PCR reaction units are arranged in parallel and spaced apart. Each of the PCR reaction units corresponds to a sample, and can individually complete all processes such as droplet generation, droplet storage and droplet spread, PCR thermal cycle and fluorescence imaging detection, with a high work efficiency. In this embodiment, the microfluidic device is provided with a plurality of groups consisting of the sample reservoir 2, the droplet generation zone 4, the droplet storage zone 6 and the collection zone 7 (waste liquid storage zone), which are independent and arranged side by side, and respectively correspond to a plurality of samples. Each of the plurality of groups consisting of the sample reservoir 2, the droplet generation zone 4, the droplet storage zone 6 and the collection zone 7 forms a whole-process processing path for a sample. The microfluidic device can complete the sample storage, droplet generation, droplet storage, PCR thermal cycle reaction, droplet detection and waste liquid storage independently for multiple samples.

The oil with a density lighter than the density of water is used in the microfluidic device, so that the droplets can sink and ensure that the droplets are not easily volatilized during heating. The microfluidic device is designed to realize a whole process of droplet generation, droplet monolayer distribution, PCR thermal cycle reaction and fluorescence imaging detection. Due to the design of the microfluidic device, the sample reservoir, the first oil injection reservoir and the second oil injection reservoir located on the upper layer 11 of the microfluidic device are integrally injection molded with the microchannel located on the lower layer of the microfluidic device, and sealed by the sealing layer in one time, thereby greatly reducing the cost of injection molding and simplifying the process flow of chip production.

Figure 10:
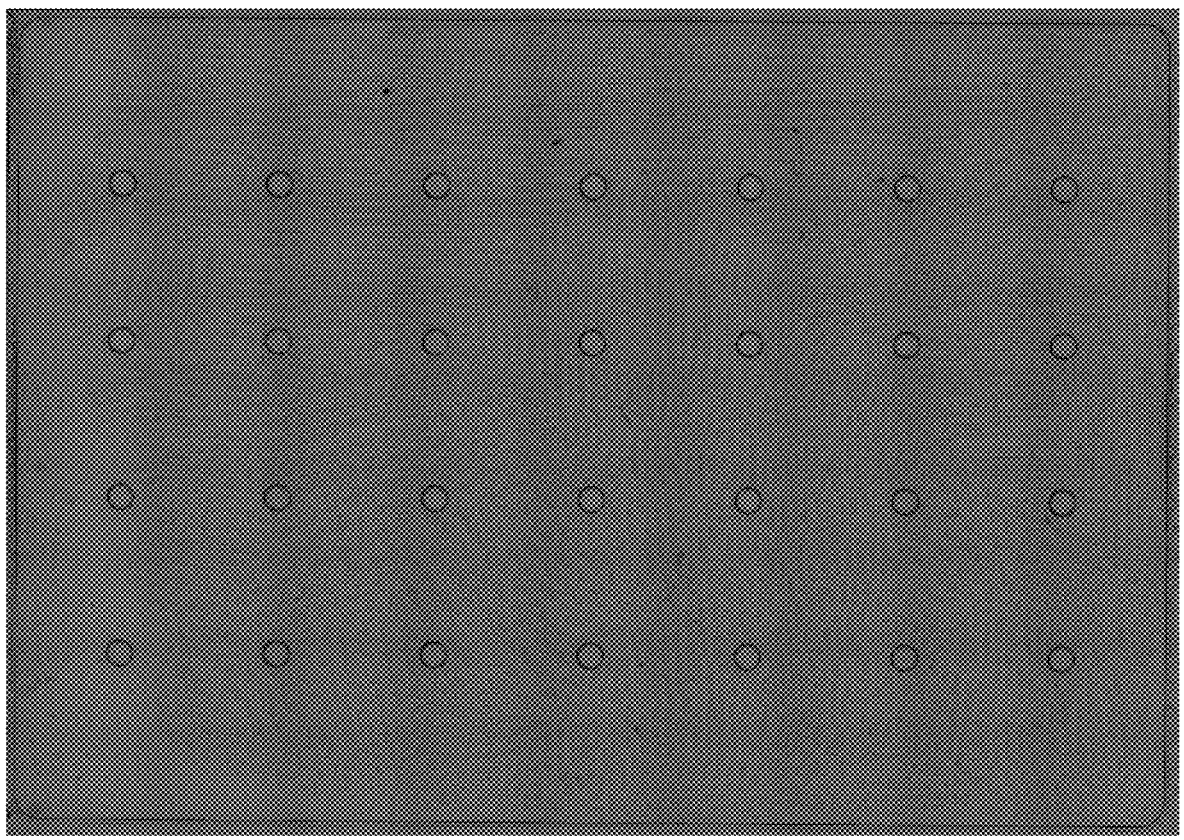
FIG. 10 is a bright field image showing droplets generated by the microfluidic device according to another embodiment of the present disclosure after PCR amplification.
Figure 11A:
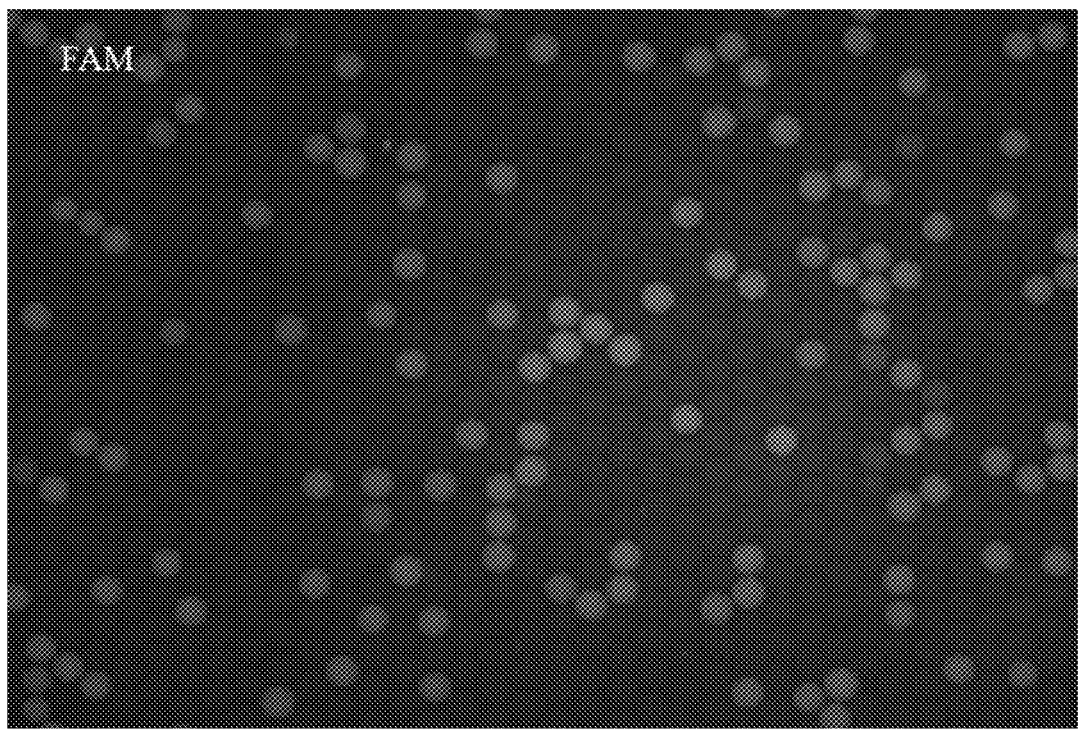
FIGS. 11a-d show droplet digital PCR amplification products respectively labeled with FAM, HEX, ROX and CY5.
Figure 11B:
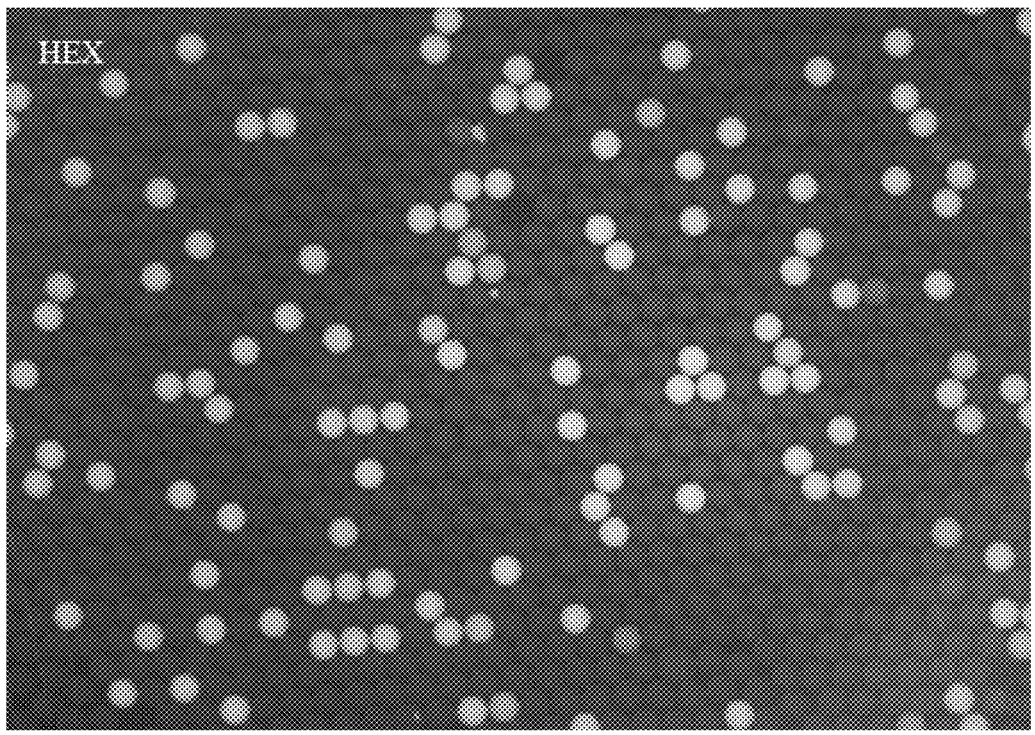
Figure 11C:
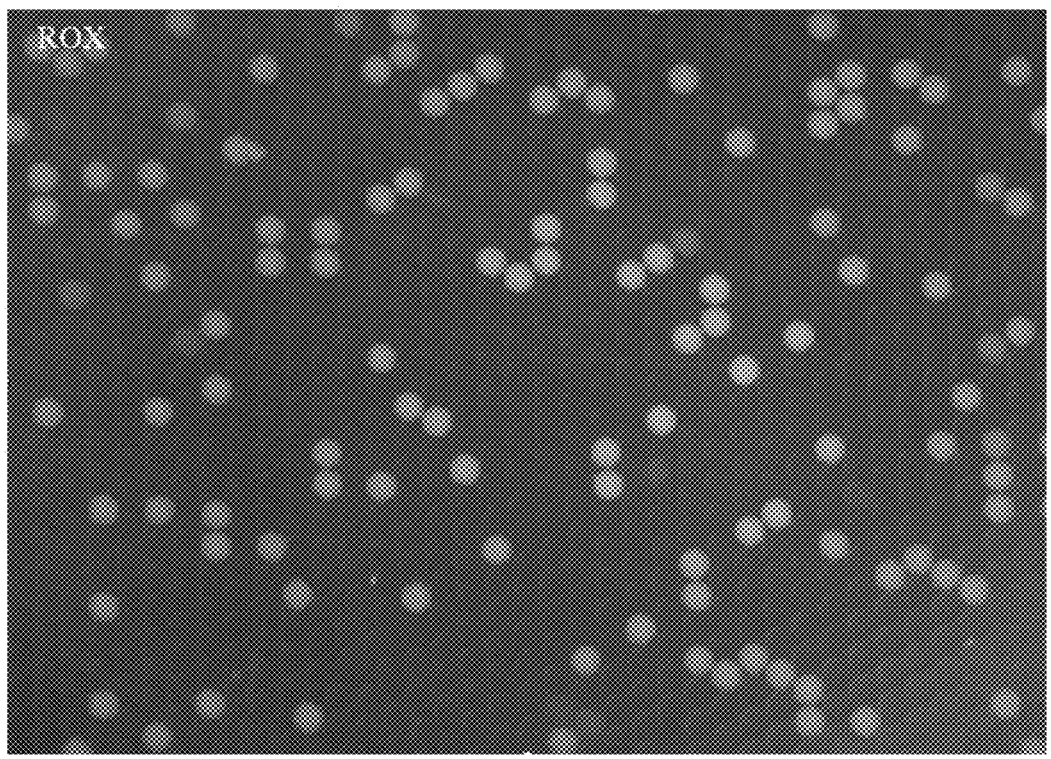
Figure 11D:
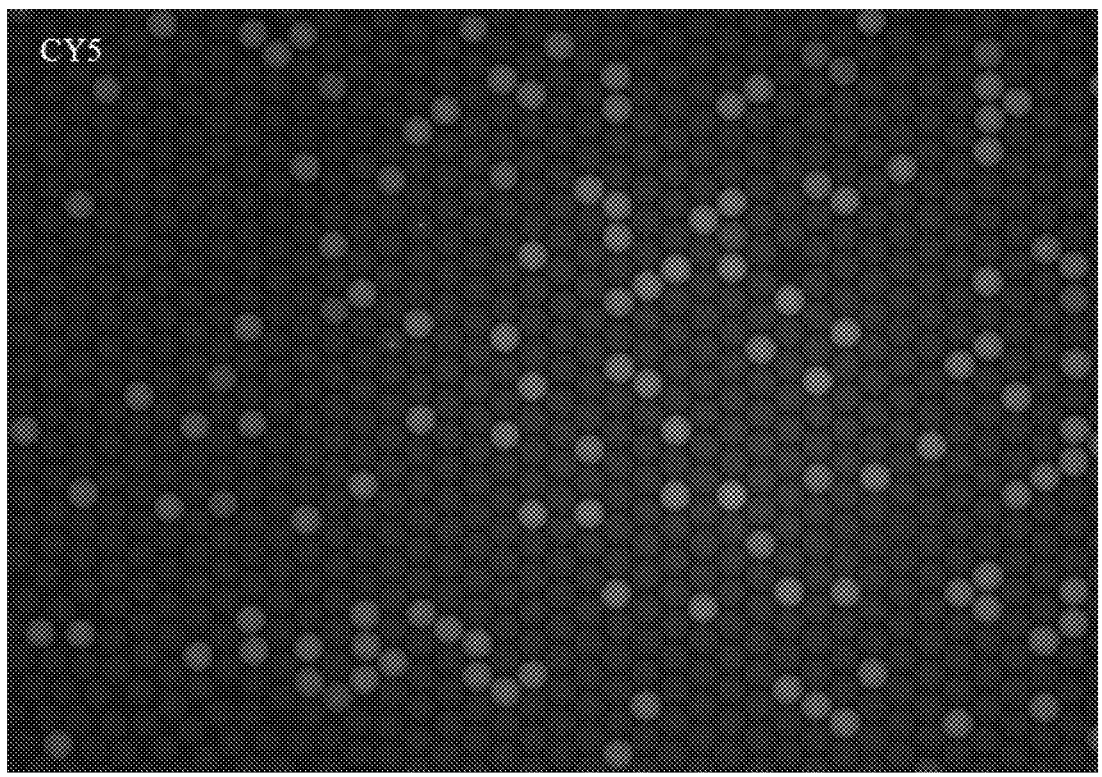

FIG. 10 depicts a bright field photo of the droplets generated by the microfluidic device after PCR amplification, and the droplets are uniform and stable after 40 high temperature PCR cycles.

FIGS. 11a-d show droplet digital PCR amplification products respectively labeled with FAM, HEX, ROX and CY5.

Described above are only preferred embodiments of the present disclosure, and are not intended to limit the present disclosure. It should be understood that any modifications, replacements and improvements made by those skilled in the art without departing from the spirit and scope of the present disclosure should fall within the scope of the present disclosure defined by the appended claims.

What is claimed is:

1. A microfluidic device, comprising:
a main body;
a sealing layer; and
a plurality of Polymerase Chain Reaction (PCR) units arranged on the main body;
wherein each of the plurality of PCR units comprises at least one microchannel arranged on a surface of the main body, a sample reservoir, an oil reservoir, a droplet generation zone, a transition zone, a droplet storage zone and a collection zone; the sample reservoir, the oil reservoir, the droplet generation zone, the transition zone, the droplet storage zone and the collection zone are communicated with each other through the at least one microchannel; the sealing layer is arranged on the surface of the main body, and is configured to seal the main body;
the sample reservoir is configured to inject a dispersed phase;
the oil reservoir and the collection zone are configured to inject a continuous phase;
the droplet generation zone is configured to generate a plurality of droplets from the dispersed phase through the continuous phase, wherein the droplet generation zone comprises a dispersed phase inlet, a sample injection channel, a dispersed phase flow channel, a plurality of sample phase branch channels and a plurality of nozzles arranged in parallel, and wherein the plurality of nozzles are communicated with the plurality of dispersed phase flow channel and the transition zone; and
the plurality of droplets are configured to flow into the oil reservoir through the nozzles and the sample phase branch channels of the droplet generation zone and stored in the oil reservoir, and then pass through the transition zone to be distributed on the droplet storage zone for PCR amplification and optical detection.

2. The microfluidic device of claim 1, wherein the main body comprises an upper layer and a lower layer;
the sample reservoir, the oil reservoir and the collection zone are arranged on the upper layer; and
the at least one microchannel, the droplet generation zone, the transition zone and the droplet storage zone are arranged on the lower layer.

3. The microfluidic device of claim 2, wherein the sample reservoir is provided with a sample injection hole; and the sample injection hole is connected to the lower layer of the main body and is communicated with the droplet generation zone.

4. The microfluidic device of claim 3, wherein the dispersed phase inlet of the droplet generation zone is provided on the lower layer of the main body, and is communicated with the sample injection hole.

5. The microfluidic device of claim 4, wherein each of the plurality of nozzles is configured as a triangle reservoir that extends to the droplet storage zone where a height of the droplet storage zone abruptly increases.

6. The microfluidic device of claim 4, wherein the transition zone comprises a first storage slot arranged on the lower layer of the main body; and
the oil reservoir is provided with a first oil injection hole; the first oil injection hole is connected to the first storage slot.

7. The microfluidic device of claim 6, wherein the droplet storage zone comprises a second storage slot and a first filtration zone; the second storage slot is arranged on the lower layer of the main body, and is communicated with the first storage slot; and the first filtration zone is arranged in the second storage slot.

8. The microfluidic device of claim 7, wherein a depth of the first storage slot is greater than or equal to 1.5 times a depth of the second storage slot, and the depth of the second storage slot is greater than or equal to 1.2 times a diameter of each of the plurality of droplets.

9. The microfluidic device of claim 8, wherein the collection zone comprises a second oil injection hole and an oil injection channel;
the second oil injection hole is connected to the lower layer of the main body; and
the oil injection channel is configured for communicating the second oil injection hole with the second storage slot.

10. The microfluidic device of claim 9, wherein the lower layer of the main body is further provided with a second filtration zone; and the second filtration zone is communicated between the oil injection channel and the second storage slot.

* * * * *